(12) United States Patent
Sirinyan et al.

(10) Patent No.: US 6,372,765 B1
(45) Date of Patent: Apr. 16, 2002

(54) PARASITICIDAL FORMULATIONS THAT CAN BE APPLIED DERMALLY

(75) Inventors: Kirkor Sirinyan, Bergisch Gladbach; Hubert Dorn, Wuppertal; Richard Kujanek, Köln, all of (DE); Klemens Krieger, Del. Magdalena Contreras (MX); Ulrich Heukamp, Kürten; Doris Hackemüller, Düsseldorf, both of (DE); Terence Hopkins, Tamborine (AU)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/435,271

(22) Filed: Nov. 5, 1999

Related U.S. Application Data

(62) Division of application No. 08/849,259, filed as application No. PCT/EP95/04667 on Nov. 27, 1995, now Pat. No. 6,001,858.

(30) Foreign Application Priority Data

Dec. 9, 1994 (DE) .......................................... 44 43 888

(51) Int. Cl.$^7$ ........................ H01N 51/00; H01N 43/28; H01N 25/02
(52) U.S. Cl. ........................ 514/336; 514/341; 514/830
(58) Field of Search ................................ 514/341, 336, 514/830

(56) References Cited

U.S. PATENT DOCUMENTS

| | | | |
|---|---|---|---|
| 4,415,563 A | | 11/1983 | Rajadhyaksha |
| 5,194,264 A | | 3/1993 | Van Tonder |
| 5,712,295 A | * | 1/1998 | Mencke et al. ............. 514/338 |
| 6,001,858 A | * | 12/1999 | Sirinyan et al. ............. 514/341 |

FOREIGN PATENT DOCUMENTS

| | | |
|---|---|---|
| DE | 2331793 | 1/1975 |
| EP | 303490 | 2/1989 |
| EP | 433909 | 6/1991 |
| EP | 483052 | 4/1992 |
| EP | 590425 | 4/1994 |
| GB | 802111 | 10/1958 |
| GB | 2194147 | 3/1988 |
| GB | 2236250 | 4/1991 |
| WO | 93/24002 | 12/1993 |

* cited by examiner

*Primary Examiner*—Alton Pryor
(74) *Attorney, Agent, or Firm*—Joseph C. Gil; Godfried R. Akorli

(57) ABSTRACT

The present invention relates to formulations for the dermal control of parasitic insects of animals, having the following composition agonists or antagonists of the nicotinergic acetylcholine receptors of insects in a concentration of from 1 to 20% by weight based on the overall weight of the formulation;

solvents from the group benzyl alcohol or optionally substituted pyrrolidones in a concentration of at least 20% by weight based on the overall weight of the formulation;

if desired, further solvents from the group consisting of cyclic carbonates or lactones in a concentration of from 5.0 up to 80% by weight based on the overall weight of the formulation;

if desired, further auxiliaries from the group thickeners, spreading agents, colorants, antioxidants, propellants, preservatives, adhesives, emulsifiers, in a concentration of from 0.025 up to 10% by weight based on the overall weight of the formulation.

3 Claims, No Drawings

PARASITICIDAL FORMULATIONS THAT CAN BE APPLIED DERMALLY

This is a Divisional of U.S. Ser. No. 08/849,259, filed Jun. 2, 1997 now 6,001,858, which is a 371 PCT/EP95/04667 filed Nov. 27, 1995.

The present invention relates to formulations for the dermal control of parasitic insects on animals by means of agonists or antagonists of the nicotinergic acetylcholine receptors of insects.

Agonists or antagonists of the nicotinergic acetylcholine receptors of insects are known. They include the nicotinyl insecticides and, very particularly, the chloronicotinyl insecticides.

PCT application WO 93/24 002 discloses that certain 1[N-(halo-3-pyridylmethyl)]-N-methylamino-1-alkylamino-2-nitroethylene derivatives are suitable for systemic use against fleas in domestic animals. According to WO 93/24 002, the nonsystemic—i.e. dermal—mode of application is unsuitable for the control of fleas on domestic animals.

New formulations for the dermal application of agonists or antagonists of the nicotinergic acetylcholine receptors of insects have now been found which are particularly suitable for dermal control of parasitic insects, such as fleas, lice or flies, on animals.

The formulations according to the invention have the following composition:

agonists or antagonists of the nicotinergic acetylcholine receptors of insects in a concentration of from 1 to 20% by weight based on the overall weight of the formulation;

solvents from the group benzyl alcohol or optionally substituted pyrrolidones in a concentration of at least 20% by weight based on the overall weight of the fomulation;

if desired, further solvents from the group consisting of cyclic carbonates or lactones in a concentration of from 5.0 up to 80% by weight based on the overall weight of the formulation;

if desired, further auxiliaries from the group thickeners, spreading agents, colorants, antioxidants, propellants, preservatives, adhesives, emulsifiers, in a concentration of from 0.025 up to 10% by weight based on the overall weight of the formulation.

Agonists or antagonists of the nicotinergic acetylcholine receptors of insects are known, for example, from European Offenlegungsschriften (European Published Applications) Nos. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; German Offenlegungsschriften (German Published Specifications) Nos. 3 639 877, 3 712 307; Japanese Offenlegungsschriften (Japanese Published Applications) Nos. 03 220 176, 02 207 083, 63 307 857, 63 287 764, 03 246 283, 04 9371, 03 279 359, 03 255 072, U.S. Pat. Nos. 5,034,524, 4,948,798, 4,918,086, 5,039,686, 5,034,404; PCT Applications Nos. WO 91/17 659, 91/4965; French Application No. 2 611 114; Brazilian Application No. 88 03 621.

Express reference is hereby made to the compounds described in these publications and to their preparation.

These compounds can be represented preferably by the general formula (I)

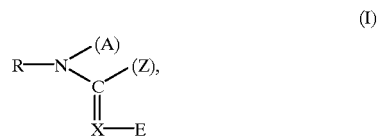

in which
R represents, hydrogen, optionally substituted radicals from the group acyl, alkyl, aryl, aralkyl, heteroaryl or heteroarylalkyl;
A represents a monofunctional group from the series hydrogen, acyl, alkyl, aryl, or represents a bifunctional group which is linked to the radical Z;
E represents an electron-withdrawing radical;
X represents the radicals —CH= or =N—, it being possible for the radical —CH=instead of a H-atom to be linked to the radical Z;
Z represents a monofunctional group from the series alkyl, —O—R, —S—R,

or represents a bifunctional group which is linked to the radical A or to the radical X Particularly preferred compounds of the formula (I) are those in which the radicals have the following meaning:

R represents hydrogen and represents optionally substituted radicals from the series acyl, alkyl, aryl, aralkyl, heteroaryl, heteroarylalkyl.

Acyl radicals which may be mentioned are formyl, alkylcarbonyl, arylcarbonyl, alkylsulphonyl, arylsulphonyl, (alkyl-(aryl)-phosphoryl, which may in turn be substituted.

As alkyl there may be mentioned $C_{1-10}$-alkyl, especially $C_{1-4}$,-alkyl, specifically methyl, ethyl, i-propyl, sec- or t-butyl, which may in turn be substituted.

As aryl there may be mentioned phenyl, naphthyl, especially phenyl.

As aralkyl there may be mentioned phenylmethyl, phenethyl.

As heteroaryl there may be mentioned heteroaryl having up to 10 ring atoms and N, O, S especially N as heteroatoms. Specifically there may be mentioned thienyl, furyl, thiazolyl, imidazolyl, pyridyl, benzothiazolyl, As heteroarylalkyl there may be mentioned heteroarylmethyl, heteroarylethyl having up to 6 ring atoms and N, O, S, especially N as heteroatoms.

Substituents which may be listed by way of example and preference are: alkyl having preferably 1 to 4, in particular 1 or 2 carbon atoms, such as methyl, ethyl, n- and i-propyl and n-, i- and t-butyl; alkoxy having preferably 1 to 4, in particular 1 or 2 carbon atoms, such as methoxy, ethoxy, n- and i- propyloxy and n-, i- and t-butyloxy; alkylthio having preferably 1 to 4, in particular 1 or 2 carbon atoms, such as methylthio, ethylthio, n- and i-propylthio and n-, i- and t-butylthio; halogenoalkyl having preferably 1 to 4, in particular 1 or 2 carbon atoms and preferably 1 to 5, in particular 1 to 3 halogen atoms, the halogen atoms being identical or different and being preferably fluorine, chlorine or bromine, especially fluorine, such as trifluoromethyl;

hydroxyl; halogen, preferably fluorine, chlorine, bromine and iodine, especially fluorine, chlorine and bromine; cyano; nitro; amino; monoalkyl- and dialkylamino having preferably 1 to 4, in particular 1 or 2 carbon atoms per alkyl group, such as methylamino, methyl-ethyl-amino, n- and i-propylamino and methyl-n-butylamino; carboxyl; carbalkoxy having preferably 2 to 4, in particular 2 or 3 carbon atoms, such as carbomethoxy and carboethoxy;,sulpho (—SO$_3$H); alkylsulphonyl having preferably 1 to 4, in particular 1 or 2 carbon atoms, such as methylsulphonyl and ethylsulphonyl; arylsulphonyl having preferably 6 or 10 aryl carbon atoms, such as phenylsulphonyl, and also heteroarylamino and heteroarylalkylamino such as chloropyridylamino and chloropyridylmethylamino.

A particularly preferably represents hydrogen and represents optionally substituted radicals from the series acyl, alkyl, aryl, which preferably have the meanings given for R. A additionally represents a bifunctional group. There may be mentioned optionally substituted alkylene having 1–14, in particular 1–2 C atoms, substituents which may be mentioned being the substituents listed earlier above, and it being possible for the alkylene groups to be interrupted by heteroatoms from the series N, O, S.

A and Z may, together with the atoms to which they are attached, form a saturated or unsaturated heterocyclic ring. The heterocyclic ring can contain a further 1 or 2 identical or different heteroatoms and/or hetero-groups. Heteroatoms are preferably oxygen, sulphur or nitrogen, and hetero-groups are preferably N-alkyl, where the alkyl in the N-alkyl group preferably contains 1 to 4, in particular 1 or 2 carbon atoms. As alkyl there may be mentioned methyl, ethyl, n- and i-propyl and n-, i- and t-butyl. The heterocyclic ring contains 5 to 7, preferably 5 or 6 ring members.

Examples of the heterocyclic ring which may be mentioned are pyrrolidine, piperidine, piperazine, hexamethyleneimine, hexahydro-1,3,5-triazine, morpholine, each of which may optionally be substituted preferably by methyl.

E represents an electron-withdrawing radical, in which context particular mention may be made of NO$_2$, CN, halogenoalkylcarbonyl such as 1,5-halogeno-C$_{1-4}$-carbonyl especially COCF$_3$.

X represents —CH= or —N=

Z represents optionally substituted radicals, alkyl, —OR, —SR,—NRR, where R and the substituents preferably have the meaning given above.

Z can form, apart from the abovementioned ring, and together with the atom to which it is attached and with the radical

instead of X a saturated or unsaturated heterocyclic ring. The heterocyclic ring can contain a further 1 or 2 identical or different heteroatoms and/or hetero-groups. The heteroatoms are preferably oxygen, sulphur or nitrogen, and the hetero-groups N-alkyl, in which case the alkyl or N-alkyl group preferably contains 1 to 4, in particular 1 or 2 carbon atoms. As alkyl there may be mentioned methyl, ethyl, n- and i-propyl and n-, i- and t-butyl. The heterocyclic ring contains 5 to 7, preferably 5 or 6 ring members.

Examples of the heterocyclic ring which may be mentioned are pyrrolidine, piperidine, piperazine, hexamethyleneimine, morpholine and N-methylpiperazine.

As compounds which may be used with very particular preference in accordance with the invention, mention may be made of compounds of the general formulae (II) and (III):

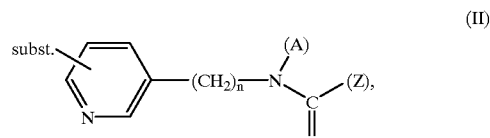

(II)

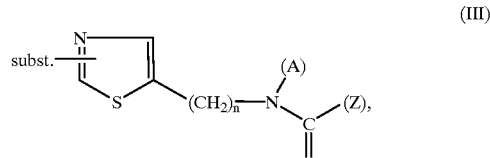

(III)

in which n represents 1 or 2, subst. represents one of the above-listed substituents, especially halogen, very particularly chlorine, A, Z, X and E have the meanings given above, Specifically, the following compounds may be mentioned:

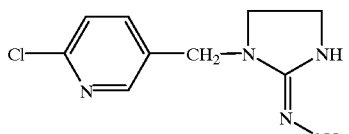

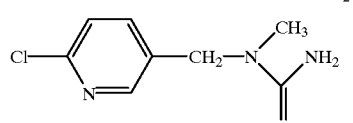

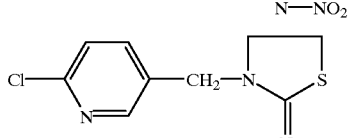

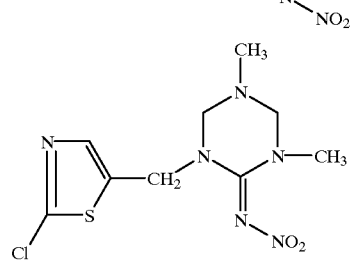

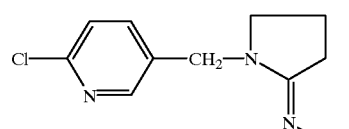

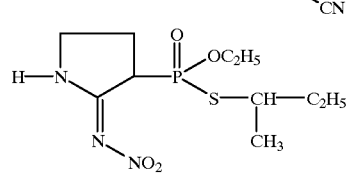

5

-continued

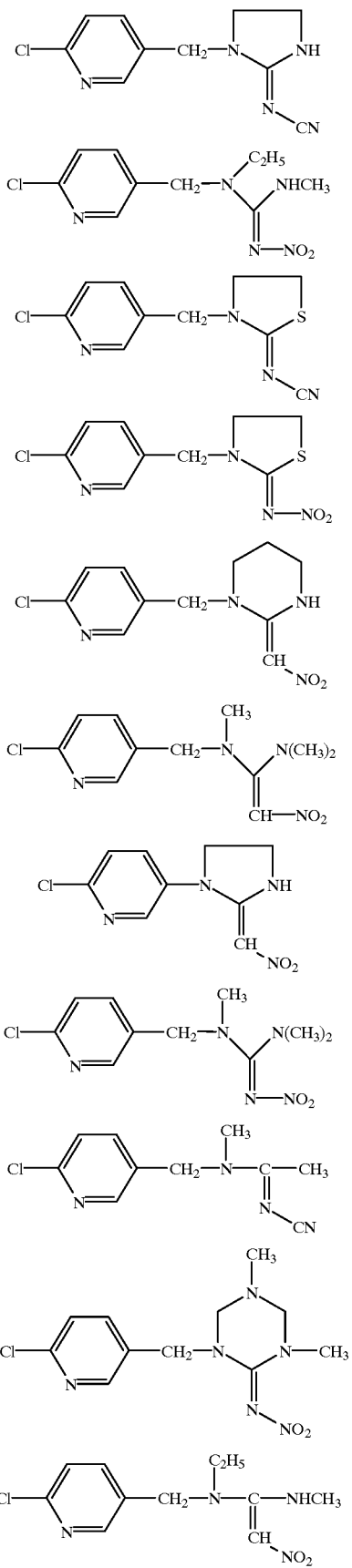

6

-continued

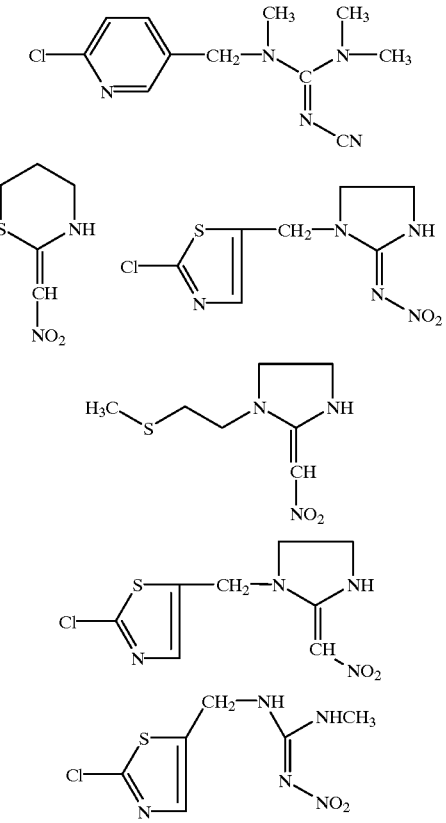

The formulations according to the invention contain the active substance in concentrations of from 0.1 to 20% by weight, preferably from 1 to 12.5% by weight.

Preparations which are diluted before use contain the active substance in concentrations of from 0.5 to 90% by weight, preferably from 1 to 50% by weight.

In general it has proved to be advantageous to administer quantities of from about 0.5 to about 50 mg, preferably from 1 to 20 mg, of active substance per body weight per day in order to achieve effective results.

Suitable solvents are:

benzyl alcohol or optionally substituted pyrrolidones such as 2-pyrrolidone, 1-($C_{2-20}$-alkyl)-2-pyrrolidone, in particular 1-ethylpyrrolidone, 1-octylpyrrolidone, 1-dodecylpyrrolidone, 1-isopropylpyrrolidone, 1-(s- or t- or n-butyl)-pyrrolidone, 1-hexylpyrrolidone, 1-($C_{2-10}$-alkenyl)-2-pyrrolidone such as 1-vinyl-2-pyrrolidone, 1-($C_{3-8}$-cycloalkyl)-2-pyrrolidone such as 1-cyclohexylpyrrolidone, 1-($C_{1-6}$-hydroxyalkyl)-2-pyrrolidone, 1-($C_{1-6}$-alkoxy-$C_{1-6}$alkyl)-2-pyrrolidone such as 1-(2-hydroxyethyl)-pyrrolidone, 1-(3-hydroxypropyl)-pyrrolidone, 1-(2-methoxyethyl)-pyrrolidone, 1-(3-methoxpropyl)-pyrrolidone, and also 1-benzylpyrrolidone. Particular mention may be made of benzyl alcohol or n-dodecyl- or n-octylpyrrolidone. These solvents can be employed either alone or in a mixture with additional solvents (cosolvents).

They are present in a concentration of at least 20% by weight preferably from 40 to 90% by weight, particularly preferably from 50 to 90% by weight.

Suitable additional solvents or cosolvents are: cyclic carbonates or lactones. As such there may be mentioned: ethylene carbonate, propylene carbonate, γ-butyrolactone.

They are present in a concentration from 5.0 up to 80% by weight preferably from 7.5 to 50% by weight, particularly preferably from 10 to 50% by weight.

Suitable further auxiliaries are: preservatives such as benzyl alcohol (not required if already present as solvent), trichlorobutanol, p-hydroxybenzoic esters, n-butanol.

Thickeners such as: inorganic thickeners such as bentonites, colloidal silicic acid, aluminium monostearate, organic thickeners such as cellulose derivatives, polyvinyl alcohols, polyvinylpyrrolidones and copolymers thereof, acrylates and methacrylates.

Colorants which may be mentioned are all colorants where use on the animal is permitted, which may be dissolved or suspended.

Auxiliaries are also spreading oils such as di-2-ethylhexyl adipate, isopropyl myristate, dipropylene glycol pelargonate, cyclic and acyclic silicone oils such as dimeticones and also c- and terpolymers thereof with ethylene oxide, propylene oxide and formalin, fatty acid esters, triglycerides, fatty alcohols.

Antioxidants are sulphites or metabisulphites such as potassium metabisulphite, ascorbic acid, butylated hydroxytoluene, butylated hydroxyanisole, tocopherol.

Light stabilizers are, for example, substances from the class of the benzophenones or Novantisol acid.

Adhesives are, for example, cellulose derivatives, starch derivatives, polyacrylates, naturally occurring polymers such as alginates, gelatin.

Auxiliaries are also emulsifiers such as nonionic surfactants, for example polyoxyethylated castor oil, polyoxyethylated sorbitan monooleate, sorbitan monostearate, glycerol monostearate, polyoxyethylstearate, alkylphenol polyglycol ethers;

ampholytic surfactants such as di-Na N-lauryl-β-iminodipropionate or lecithin;

anionic surfactants, such as Na-lauryl sulphate, fatty alcohol ether sulphates, mono/dialkyl-polyglycol ether orthophosphoric ester monoethanolamine salt;

cationic surfactants such as cetyltrimethylammonium chloride.

Further auxiliaries are agents with which the formulations according to the invention can be sprayed or squirted onto the skin. These are the conventional propellent gases required for spray cans, such as propane, butane, dimethyl ether, $CO_2$ or halogenated lower alkanes, or mixtures thereof with one another.

While being of low toxicity to warm-blooded species, the formulations according to the invention are suitable for the control of parasitic insects which are encountered in animal keeping and animal breeding in domestic and productive animals and in zoo and laboratory animals and animals used for experimentation and in the pursuit of hobbies. In this content they are active against all or individual stages of development of the pests and against resistant and normally sensitive species of the pests.

The pests include:

from the order of the Anoplura e.g. Haematopinus spp., Linognathus spp., Solenopotes spp., Pediculus spp., Pthirus spp.;

from the order of the Mallophaga e.g. Trimenopon spp., Menopon spp., Eomenacanthus spp., Menacanthus spp., Trichodectes spp., Felicola spp., Damalinea spp., Bovicola spp;

from the order of the Diptera e.g. Chrysops spp., Tabanus spp., Musca spp., Hydrotaea spp., Muscina spp., Haematobosca spp., Haematobia spp., Stomoxys spp., Fannia spp., Glossina spp., Lucilia spp., Calliphora spp., Auchmeromyia spp., Cordylobia spp., Cochliomyia spp., Chrysomyia spp., Sarcophaga spp., Wohlfartia spp., Gasterophilus spp., Oesteromyia spp., Oedemagena spp., Hypoderma spp., Oestrus spp., Rhinoestrus spp., Melophagus spp., Hippobosca spp.

From the order of the Siphonaptera e.g. Ctenocephalides spp., Echidnophaga spp., Ceratophyllus spp.

Particular mention may be made of the action against Siphonaptera, especially against fleas.

The productive and breeding animals include mammals such as, for example, cattle, horses, sheep, pigs, goats, camels, water buffalo, donkeys, rabbits, fallow deer, reindeer, fur-bearing animals such as, for example, mink, chinchilla or racoon, birds such as, for example, chickens, geese, turkeys, ducks.

Laboratory animals and those for experimentation include mice, rats, guinea pigs, golden hamsters, dogs and cats.

The hobby animals include dogs and cats.

Administration can be effected both prophylactically and therapeutically.

In the shaped articles according to the invention, it is also possible for further active substances to be present. The further active substances include insecticides such as phosphorus-containing compounds, i.e. phosphates or phosphonates, natural or synthetic pyrethroides, carbamates, amidines, juvenile hormones and juvenoid synthetic active substances, and chitin synthesis inhibitors such as diaryl ethers and benzoylureas.

The phosphates or phosphonates include:

0-ethyl-0-(8-quinolyl)phenyl thiophosphate (quintiofos), 0,0-diethyl 0-(3-chloro4methyl-7-coumarinyl)-thiophosphate (coumaphos), 0,0-diethyl 0-phenylglycoxylonitrile oxime thiophosphate (phoxim), 0,0-diethyl 0-cyanochlorobenzaldoxime thiophosphate (chlorphoxim), 0,0-diethyl 0-(4-bromo-2,5-dichlorophenyl) phosphorothionate (bromophos-ethyl), 0,0,0'0',-tetraethyl S,S'-methylene-di(phosphorodithionate) (ethion), 2,3-p-dioxanedithiol S,S-bis(0.0-diethyl phosphorodithionate), 2-chloro-1-(2,4-dichlorophenyl)-vinyl diethyl phosphate (chlorfenvinphos), 0,0-dimethyl 0-(3-methylthiophenyl) thionophosphate (fenthion).

The carbamates include:

2-isopropoxyphenyl methylcarbamate (propoxur), 1-naphthyl N-methylcarbamate (carbaryl).

The synthetic pyrethroides include 3-[2-(4-chlorophenyl)-2-chlorovinyl]-2,2-dimethyl-cyclo-propanecarboxylic acid (α-cyano4fluoro-3-phenoxy)-benzyl ester (flumethrin), α-cyano(4-fluoro-3-phenoxy)-benzyl 2,2-dimethyl-3-(2,2-dichlorovinyl)-cyclopropanecarboxylate (cyfluthrin) an its enantiomers and stereomers, α-cyano-3-phenoxybenzyl (±)-cis, trans-3-(2,2-dichlorovinyl)-2,2-dimethylcyclopropanecarboxylate (deltamethrin), α-cyano-3-phenoxybenzyl 2,2-dimethyl-3-(2,2-dichlorovinyl) cyclopropanecarboxylate (cypermethrin), 3-phenoxybenzyl (±)-cis, trans-3-(2,2-dichlorovinyl)-2,2-dimethylcyclopropanecarboxylate (permethrin), α-cyano-3-phenoxy-benzyl α-(p-Cl-phenyl)-isovalrate (fenvalerate), 2-cyano-3-phenoxybenzyl 2-(2-chloro-α,α,α-trifluoro-p-toluidino)-3-methylbutyrate (fluvalinate).

The amidines include:
3-methyl-2[2,4-dimethyl-phenylimino]-thiazoline,
2-(4-chloro-2-methylphenylimino)-3-methylthiazolidine,
2-(4-chloro-2-methylphenylimino)-3-(isobutyl-1-enyl)-thiazolidine
1,5-bis-(2,4-dimethylphenyl)-3-methyl-1,3,5-triazapenta-1,4-diene (amitraz).

Cyclic macroliths such as invermectins and abamectins. In this context there may be mentioned, for example, 5-0-dimethyl-22,23-dihydroavermectin-$A_{1a}$,-22,23-dihydroavermectin $B_{1a}$, and 22,23-dihydroavermectin $B_{1a}$ (cf. for example WHO.

F. A. Series 27, pp. 27—73 (1991)). In juvenile hormone and juvenile hormone-like substances include, in particular, compounds of the following formulae:

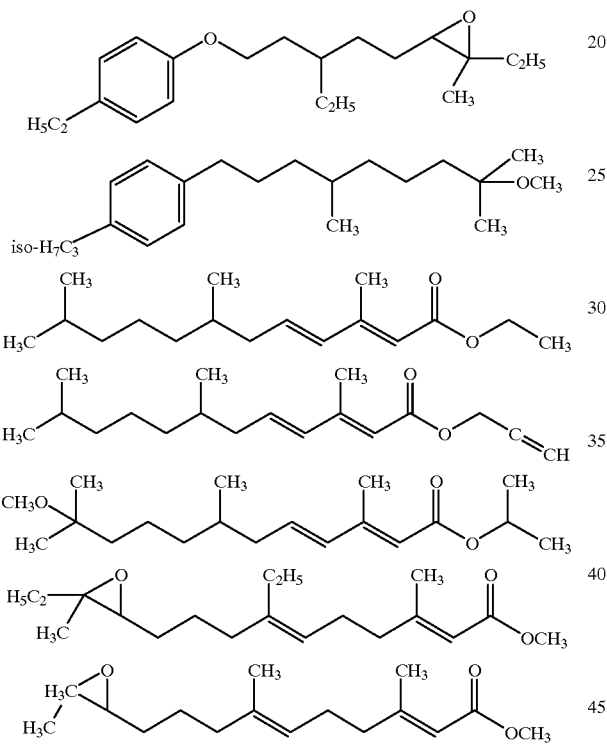

The substituted diaryl ethers include, in particular

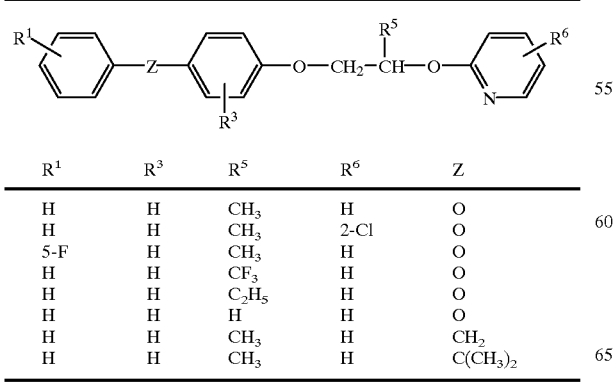

| $R^1$ | $R^3$ | $R^5$ | $R^6$ | Z |
|---|---|---|---|---|
| H | H | $CH_3$ | H | O |
| H | H | $CH_3$ | 2-Cl | O |
| 5-F | H | $CH_3$ | H | O |
| H | H | $CF_3$ | H | O |
| H | H | $C_2H_5$ | H | O |
| H | H | H | H | O |
| H | H | $CH_3$ | H | $CH_2$ |
| H | H | $CH_3$ | H | $C(CH_3)_2$ |

The benzoyl ureas include compounds of the formula

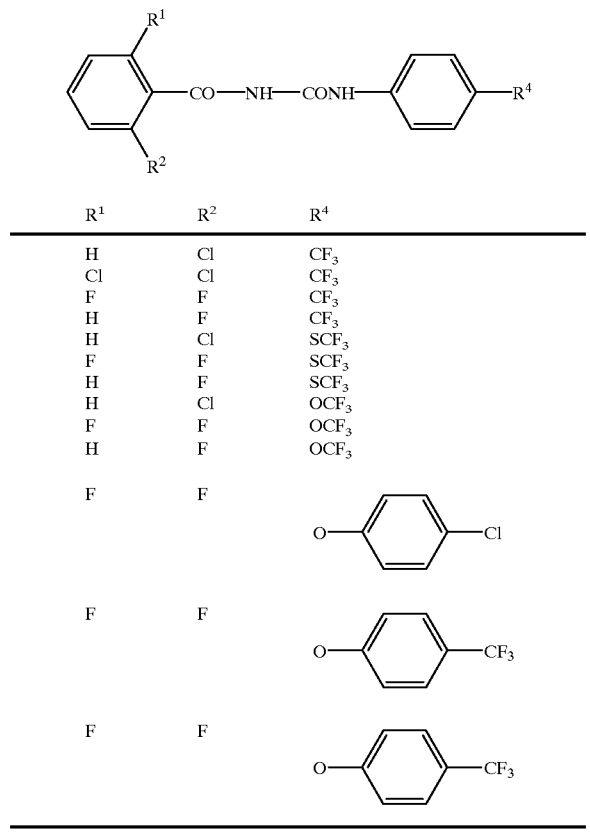

| $R^1$ | $R^2$ | $R^4$ |
|---|---|---|
| H | Cl | $CF_3$ |
| Cl | Cl | $CF_3$ |
| F | F | $CF_3$ |
| H | F | $CF_3$ |
| H | Cl | $SCF_3$ |
| F | F | $SCF_3$ |
| H | F | $SCF_3$ |
| H | Cl | $OCF_3$ |
| F | F | $OCF_3$ |
| H | F | $OCF_3$ |
| F | F | ![-O-C6H4-Cl] |
| F | F | ![-O-C6H4-CF3] |
| F | F | ![-O-C6H4-CF3] |

The triazines include compounds of the formula

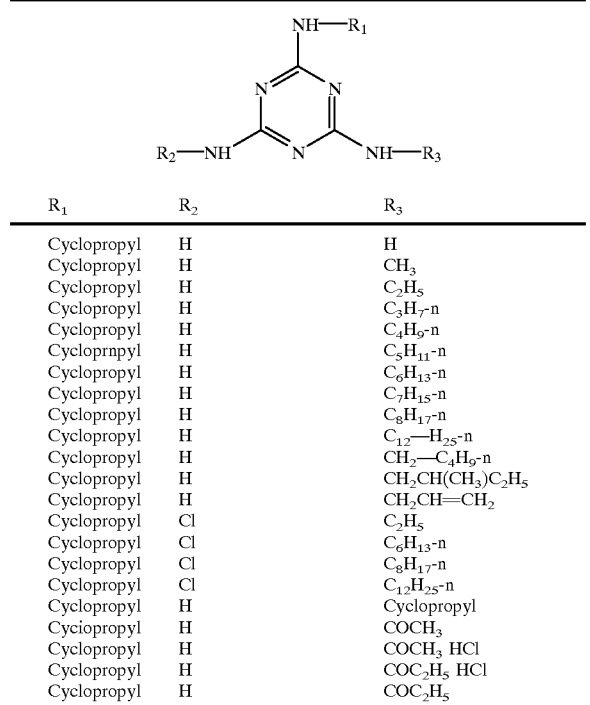

| $R_1$ | $R_2$ | $R_3$ |
|---|---|---|
| Cyclopropyl | H | H |
| Cyclopropyl | H | $CH_3$ |
| Cyclopropyl | H | $C_2H_5$ |
| Cyclopropyl | H | $C_3H_7$-n |
| Cyclopropyl | H | $C_4H_9$-n |
| Cycloprnpyl | H | $C_5H_{11}$-n |
| Cyclopropyl | H | $C_6H_{13}$-n |
| Cyclopropyl | H | $C_7H_{15}$-n |
| Cyclopropyl | H | $C_8H_{17}$-n |
| Cyclopropyl | H | $C_{12}$—$H_{25}$-n |
| Cyclopropyl | H | $CH_2$—$C_4H_9$-n |
| Cyclopropyl | H | $CH_2CH(CH_3)C_2H_5$ |
| Cyclopropyl | H | $CH_2CH=CH_2$ |
| Cyclopropyl | Cl | $C_2H_5$ |
| Cyclopropyl | Cl | $C_6H_{13}$-n |
| Cyclopropyl | Cl | $C_8H_{17}$-n |
| Cyclopropyl | Cl | $C_{12}H_{25}$-n |
| Cyclopropyl | H | Cyclopropyl |
| Cyclopropyl | H | $COCH_3$ |
| Cyclopropyl | H | $COCH_3$ HCl |
| Cyclopropyl | H | $COC_2H_5$ HCl |
| Cyclopropyl | H | $COC_2H_5$ |

-continued

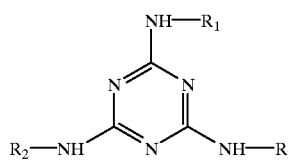

| R₁ | R₂ | R₃ |
|---|---|---|
| Cyclopropyl | H | $COC_3H_7$-n |
| Cyclopropyl | H | $COC_3H_7$-i |
| Cyclopropyl | H | $COC_4H_9$-t HCl |
| Cyclopropyl | H | $COC_4H_9$-n |
| Cyclopropyl | H | $COC_6H_{13}$-n |
| Cyclopropyl | H | $COC_{11}$—$H_{23}$-n |
| Cyclopropyl | $COCH_3$ | $COC_2H_5$ |
| Cyclopropyl | $COC_3H_7$-n | $COC_6H_{13}$-n |
| Cyclopropyl | $COCH_3$ | $COC_3H_7$-n |
| Cyclopropyl | $COC_2H_5$ | $COC_3H_7$-n |
| Cyclopropyl | H | COCyclopropyl |
| Cyclopropyl | COCyclopropyl | COCyclopropyl |
| Cyclopropyl | $COCH_3$ | $COCH_3$ |
| Isopropyl | H | H |
| Isopropyl | H | $COCH_3$ |
| Isopropyl | H | $COC_3H_7$-n |
| Cyclopropyl | H | $CONHCH_3$ |
| Cyclopropyl | H | $CONHC_3H_7$-i |
| Cyclopropyl | $CONHCH_3$ | $CONHCH_3$ |
| Cyclopropyl | H | $SCNHCH_3$ |
| Cyclopropyl | H | $CONHCH_2CH=CH_2$ |
| Cyclopropyl | $CONHCH_2CH=CH_2$ | $CONHCH_2CH=CH_2$ |
| Cyclopropyl | $CSNHCH_3$ | $CSNHCH_3$ |

Particular emphases should be given to the further active substances having the common names propoxur, cyfluthrin, flumethrin, pyriproxyfen, methoprene, diazinon, amitraz, fenthion and levamisol.

In the examples which follow, the active substance employed is 1-[(6chloro-3-pyridinyl) methyl]-N-nitro-2-imidazolidinium (common name imidacloprid).

We claim:

1. Compositions for the dermal control of parasitic insects on animals, comprising:
   solvents from the group benzyl alcohol and optionally substituted pyrrolidones in a concentration of at least 20% by weight based on the overall weight of the compositions; and
   additional solvents from the group consisting of cyclic carbonates and lactones in a concentration of from 5.0 up to 80% by weight based on the overall weight of the compositions; and
   optionally, auxiliaries selected from the group of thickeners, spreading agents, colorants, antioxidants, propellants, preservatives, adhesives, and emulsifiers, in a concentration of from 0.025 up to 10% by weight based on the overall weight of the composition.

2. A process for the production of the compositions according to claim 1, characterized in that the compound is mixed with said solvent(s), and auxiliaries are optionally added.

3. A method for the dermal control of parasitic insects on animals, comprising applying to an animal in need thereof a physiologically active amount of the composition according to claim 1.

* * * * *

UNITED STATES PATENT AND TRADEMARK OFFICE
CERTIFICATE OF CORRECTION

PATENT NO. : 6,372,765 B1
DATED : April 16, 2002
INVENTOR(S) : Kirkor Sirinyan et al.

It is certified that error appears in the above-identified patent and that said Letters Patent is hereby corrected as shown below:

Column 12,
Line 10, insert

-- agonists or antagonists of the nicotinergic acetylcholine receptors of insects in a concentration of from about 1 to about 20% by weight based on the overall weight of the compositions containing an effective amount of the compound of formula (I)

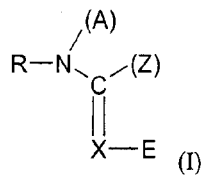

in which

R     represents, hydrogen, optionally substituted radicals from the group acyl, alkyl, aryl, aralkyl, heteroaryl or heteroarylalkyl;

A     represents a monofunctional group from the series hydrogen, acyl, alkyl, aryl, or represents a bifunctional group which is linked to the radical Z;

E     represents an electron-withdrawing radical;

X     represents the radicals -CH= or =N-, it being possible for the radical -CH= instead of a H-atom to be linked to the radical Z;

UNITED STATES PATENT AND TRADEMARK OFFICE
CERTIFICATE OF CORRECTION

PATENT NO.   : 6,372,765 B1
DATED        : April 16, 2002
INVENTOR(S)  : Kirkor Sirinyan et al.

It is certified that error appears in the above-identified patent and that said Letters Patent is hereby corrected as shown below:

Column 12, line 10, cont'd,

Z    represents a monofunctional group from the series alkyl, =O=R, -S-R,

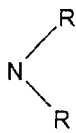

or represents a bifunctional group which is linked to the radical A or to the radical X, excluding

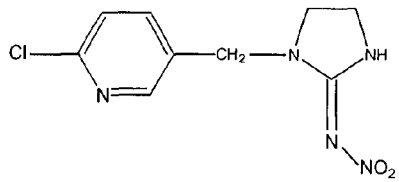

and --

Signed and Sealed this

Thirtieth Day of March, 2004

JON W. DUDAS
*Acting Director of the United States Patent and Trademark Office*